(12) United States Patent
Bornstein

(10) Patent No.: US 7,255,560 B2
(45) Date of Patent: Aug. 14, 2007

(54) LASER AUGMENTED PERIODONTAL SCALING INSTRUMENTS

(75) Inventor: Eric Bornstein, Natick, MA (US)

(73) Assignee: Nomir Medical Technologies, Inc., Natick, MA (US)

(*) Notice: Subject to any disclaimer, the term of this patent is extended or adjusted under 35 U.S.C. 154(b) by 97 days.

(21) Appl. No.: 10/723,031

(22) Filed: Nov. 26, 2003

(65) Prior Publication Data
US 2004/0202982 A1   Oct. 14, 2004

Related U.S. Application Data

(60) Provisional application No. 60/430,294, filed on Dec. 2, 2002.

(51) Int. Cl.
*A62C 17/00* (2006.01)
(52) U.S. Cl. .......................... 433/143; 433/29
(58) Field of Classification Search ................ 433/29, 433/143, 144, 215, 141, 142
See application file for complete search history.

(56) References Cited

U.S. PATENT DOCUMENTS

| | | |
|---|---|---|
| 4,669,466 A | 6/1987 | L'Esperance |
| 4,917,084 A | 4/1990 | Sinofsky |
| 4,945,239 A | 7/1990 | Wist et al. |
| 5,090,908 A * | 2/1992 | Teumim-Stone ............ 433/215 |
| 5,196,004 A | 3/1993 | Sinofsky |
| 5,328,365 A * | 7/1994 | Jacoby ........................ 433/29 |
| 5,464,436 A | 11/1995 | Smith |
| 5,595,568 A | 1/1997 | Anderson et al. |
| 5,683,380 A | 11/1997 | Eckhouse |
| 5,693,043 A | 12/1997 | Kitterell et al. |
| 5,735,844 A | 4/1998 | Anderson et al. |
| 5,853,407 A | 12/1998 | Miller |
| 5,954,710 A | 9/1999 | Paolini |
| 6,015,404 A | 1/2000 | Altshuler et al. |
| 6,039,565 A * | 3/2000 | Chou et al. ................. 433/215 |
| 6,080,146 A | 6/2000 | Altshuler et al. |
| 6,090,788 A | 7/2000 | Lurie |

(Continued)

FOREIGN PATENT DOCUMENTS

WO   WO91/13652   9/1991

(Continued)

OTHER PUBLICATIONS

Liang, et al., Wavelength Dependence of Cell Cloning Efficiency after Optical Trapping, Biophy.J. Mar. 1996, pp. 1529-1533, vol. 70.

(Continued)

*Primary Examiner*—Melba Bumgarner
(74) *Attorney, Agent, or Firm*—McDermott Will & Emery LLP

(57) ABSTRACT

An instrument is provided to enables a dental professional to subject a surgical site simultaneously to (1) mechanical cutting, scraping and grinding, and (2) laser trimming and cauterization. As a result, simultaneous removal of diseased tissue and destruction of residual bacteria is enabled. The instrument comprises a hollow shank having, a rearward fitting, and a forward contact head. Within shank extends a fiber optic bundle. As shown, laser energy is delivered from a laser through the fitting and the laser bundle to the contact head. In the contact head are a surgical blade and an exit window for the laser energy.

2 Claims, 1 Drawing Sheet

U.S. PATENT DOCUMENTS

| | | | |
|---|---|---|---|
| 6,104,959 | A | 8/2000 | Spertell |
| 6,149,644 | A | 11/2000 | Xie |
| 6,235,016 | B1 | 5/2001 | Stewart |
| 6,273,884 | B1 | 8/2001 | Altshuler et al. |
| 6,283,986 | B1 | 9/2001 | Johnson |
| 6,387,089 | B1 | 5/2002 | Kreindel et al. |
| 6,508,813 | B1 | 1/2003 | Altshuler et al. |
| 6,514,243 | B1 | 2/2003 | Eckhouse et al. |
| 6,517,532 | B1 | 2/2003 | Altshuler et al. |
| 6,561,802 | B2 * | 5/2003 | Alexander .................. 433/29 |
| 6,605,080 | B1 | 8/2003 | Altshuler et al. |
| 6,648,904 | B2 | 11/2003 | Altshuler et al. |
| 6,662,054 | B2 | 12/2003 | Kreindel et al. |
| 6,702,808 | B1 | 3/2004 | Kreindel |
| 6,815,209 | B2 | 11/2004 | Baeummer et al. |
| 6,824,542 | B2 | 11/2004 | Jay |
| 6,878,144 | B2 | 4/2005 | Altshuler et al. |
| 6,887,261 | B1 | 5/2005 | Peyman |
| 6,889,090 | B2 | 5/2005 | Kreindel |
| 6,890,346 | B2 | 5/2005 | Ganz et al. |
| 6,902,563 | B2 | 6/2005 | Wilkens et al. |
| 6,939,344 | B2 | 9/2005 | Kreindel |
| 6,960,201 | B2 | 11/2005 | Cumbie |
| 7,041,100 | B2 | 5/2006 | Kreindel |
| 7,060,061 | B2 | 6/2006 | Altshuler et al. |
| 7,118,563 | B2 | 10/2006 | Weckwerth et al. |
| 2003/0023284 | A1 | 1/2003 | Garstein et al. |
| 2003/0059379 | A1* | 3/2003 | Andersen et al. ............. 424/49 |
| 2003/0208249 | A1 | 11/2003 | Chen |
| 2004/0093042 | A1 | 5/2004 | Altshuler et al. |
| 2004/0210276 | A1 | 10/2004 | Altshuler et al. |
| 2005/0065577 | A1 | 3/2005 | McArthur et al. |
| 2005/0075703 | A1 | 4/2005 | Larsen |
| 2005/0107853 | A1 | 5/2005 | Krespi et al. |
| 2006/0004425 | A1 | 1/2006 | Cumbie |
| 2006/0200213 | A1 | 9/2006 | McDaniel |

FOREIGN PATENT DOCUMENTS

| | | |
|---|---|---|
| WO | WO 01/74265 | 10/2001 |
| WO | WO 02/086550 | 10/2002 |
| WO | WO 03/049892 | 6/2003 |
| WO | WO 03/079883 | 10/2003 |
| WO | WO 03/086215 | 10/2003 |
| WO | WO 2004/000150 | 12/2003 |
| WO | WO 2004/024144 | 3/2004 |
| WO | WO 2004/058352 | 7/2004 |
| WO | WO 2006/076506 | 7/2006 |

OTHER PUBLICATIONS

Neuman, et al., Characterization of Photodamage to *Escherichia coli* in Optical Traps, Biophy J. Nov. 1999, pp. 2865-2863, vol. 77.

Neuman, K.C., Single Molecule Study of RNA Polymerase Transcription Under Load, Ph.D. Dissertation presented to Princeton University, Nov. 2002, 120 pp.

Karu, et al., Effects of Near-Infrared Laser and Superluminous Diode Irradiation on *Escherichia coli* Division Rate, IEEE Journal of Quantum Elect, Dec. 1990, vol. 26, No. 112.

\* cited by examiner

LASER AUGMENTED PERIODONTAL SCALING INSTRUMENTS

CROSS REFERENCE TO RELATED APPLICATIONS

The present application relies on the filing date of U.S. provisional patent application 60/430,294, filed Dec. 2, 2002 in the name of the applicant hereof.

STATEMENT REGARDING FEDERALLY SPONSORED RESEARCH AND DEVELOPMENT

Not Applicable

BACKGROUND OF THE INVENTION

1. Field of the Invention

The present invention relates to dental instruments and, more particularly, to laser augmented periodontal scaling instruments (LAPSI). Such instruments are particularly applicable in the treatment of periodontal pockets and other periodontal disease.

2. Description of the Prior Art

The Periodontal Pocket and Periodontitis

A periodontal pocket is a gingival sulcus that has been pathologically deepened beyond three millimeters by an apical migration of the gingival attachment. This apical migration of the gingival attachment occurs because the supporting periodontal tissues have been compromised or destroyed and ultimately leads to the loosening of the tooth and eventual dental exfoliation if left unchecked and untreated. There are many clinical signs associated with the periodontal pocket, including thickened marginal gingiva, gingival bleeding, production of pus, tooth mobility, tooth migration, and pain. To locate and correctly diagnose a periodontal pocket, a comprehensive probing of the tooth must be done with a periodontal probe, and x-rays must be examined, to locate the depth of the pocket and extent of the destruction.

The etiology and pathogenesis of the periodontal pocket and hence periodontal disease is well understood. The main culprits are pathogenic bacteria that create a localized immune and inflammatory response to the microbial insult, mitigating massive and insidious local tissue destruction. These pathogenic bacteria can be found in the periodontal architecture of the soft tissue of the pocket, the exposed cementum, or dentin of the tooth. As inflammatory changes begin to occur in the connective tissues of the gingival sulcus (because of this bacterial insult), deleterious cellular exudate and microbial infiltration begin to degrade the gingival fibers connecting the tissue to the tooth (the periodontal ligament). As the collagen fibers of this attachment are broken down, the area is filled with inflammatory cells and edematous fluids. As this attachment tissue loses its cohesiveness, it detaches from the surface of the cementum and migrates apically forming the periodontal pocket. This progression will create an area around the tooth that cannot be adequately cleansed with local plaque removal techniques, will harbor large amounts of the causative pathogenic bacteria, and establish a continuous repeating process that once begun will ultimately lead to periodontal disease and tooth loss.

The periodontal pocket is generally considered to be a chronic inflammatory lesion that is constantly trying to repair itself with new collagen formation and other tissue components. The single factor preventing repair of the lesion (periodontal pocket) is the never ending presence and persistence of the microbial insult on the tissues. This bacterial insult constantly and chronically stimulates immune and inflammatory cells causing degeneration of any newly formed tissue, along with further degrading existing healthy tissue. As the collagenous tissues imbedded in the root surface of the tooth (cementum) are destroyed, the pathogenic bacteria can invade the actual root surface of the tooth, as far as the cementodentinal junction, and may also enter the dentinal tubules. As the periodontal pocket migrates apically, bone loss becomes apparent. The loss of the bony architecture around a periodontal pocket is also an inflammatory, proliferative and degenerative process.

Bone loss and destruction apical to the periodontal pocket is a direct consequence of the bacterial penetration into and the inflammation associated with the base of the pocket. The change and more aggressive nature of the disease from a periodontal pocket to periodontitis with bony destruction occurs with a shift in the composition of the bacterial plaque in the area. As bony destruction begins, this shift is seen as a higher presence of motile and spirochete bacteria and a lesser presence of coccoid and straight rods. These motile bacteria further invade or bore into the supporting structures (collagen and bone) causing deeper immune and inflammatory responses- Once this bacterially fueled inflammatory process reaches the bone surrounding the periodontal ligament, bony destroying cells (osteoclasts) and white blood cells increase in number in the area, and bony destruction begins.

Conventional Periodontal Pocket Treatment

To successfully treat the periodontal pocket and periodontal disease, the local inflammation and the cause of the local inflammation must be eliminated. Once the cause of the inflammatory response is eliminated, a healthy individual will show remarkable capacity to heal his/her own periodontal tissues. With this statement as a universal given in the etiology of periodontal disease, the removal of the offending periodontal plaque and all of the inflammatory components that come with it is the primary focus of successful periodontal therapy. If this can be accomplished with minimal tissue manipulation (flap surgery only if absolutely necessary), keeping the area free of foreign bodies (removing calculus and not introducing time released solid or gelatinous drug delivery systems), and the almost complete removal of the offending microorganisms associated with plaque, healing will be improved and profound. This profound healing can be seen with new collagenous and epithelial attachments known as new periodontal ligament attachment. These occur only in areas not previously exposed to the pocket, and long junctional epithelium (a strong epithelial adaptation to the root surface) occurs in areas that were exposed to the pocket. Periodontal medicine has traditionally employed a variety of armamentarium and instrumentarium to accomplish this goal. Periodontal instruments have been invented and designed over the years for the specific goal of calculus removal, root planing and debridement, and removal of diseased periodontal tissues. In particular, periodontal scaling, root planing and curettage instruments are the armamentarium of choice to remove dental plaque, calculus, diseased cementum, and diseased pocket soft tissues. Below is a list of the most commonly employed names and uses of such armamentaria:

1) Sickle scalers to remove supragingival plaque and calculus: These have a flat surface with two cutting edges that converge at a cutting tip.

2) Curettes (Gracey curettes/scalers are most prevalent) for subgingival scaling, root planing, and soft tissue debridement: These have cutting edges that are set at a 90 degree angle to the lower end of the shank and come in a variety of shapes and sizes.

3) Hoe, chisel and file scalers to further aid in calculus and diseased cementum removal.

4) Ultrasonic instruments: These vibrate at from 20,000 to 45,000 hz in an effort to aid in the removal of calculus, deposits and plaque removal. Many ultrasonic instruments also pump water or local antimicrobials into the area to act as a flushing mechanism. Studies comparing ultrasonic and hand instrumentation used for periodontal scaling showed no significant statistical difference in probing depth reduction, bleeding on probing, and subgingival microflora reduction. Both hand instrumentation and ultrasonic scalers appear to have equal efficacy and treatment outcome. Also, as the etiology of periodontal disease has become more clear (ie. that it is bacterially driven), a number of pharmacological interventions have recently been tested and adapted as an adjunct to traditional mechanical treatment These pharmacological agents take the form of time released antimicrobial agents delivered into the periodontal pocket after mechanical debridement, to help eradicate pathogenic bacteria and hence decrease the tissues inflammatory response. However, they have significant limitations.

1) They must be sure to reach the intended site of action (a deep 3-dimensional periodontal pocket).

2) They must remain at an adequate concentration to be effective.

3) They must last for a sufficient duration of time to be effective.

To remain at an adequate concentration and last for a sufficient duration of time, there is a necessity for the intrasulcular delivery system of the antimicrobials to fill the physical space of the periodontal pocket with resorbable gels, resorbable spheres, impregnated chips for the duration of the therapy or drug delivery (usually 7 to 10 days). This in and of itself will be a foreign body preventing the immediate healing process and progress of long junctional epithelium formation at the tooth pocket interface after mechanical debridement. Also, the majority of local antimicrobials used are bacteriostatic in nature and never fully eliminate periodontal pathogens from the treatment site. This can only lead to long term resistant strains forming in the periodontal pocket in response to the sublethal effect of the antimicrobial.

SUMMARY OF THE INVENTION

It has been established that diode fiber laser debridement in conjunction with mechanical scaling (with and without an exogenous chromophore) is an effective adjunctive treatment modality for periodontal disease. The present invention couples a diode laser array to the scalers with an impregnated optical fiber will simultaneously accomplish two tasks during the periodontal therapy. The laser augmented scaling instruments will effectively remove 99% of the pathogenic bacteria from the periodontal pocket (effectively eliminating and stopping the inflammatory response) while the traditional scaling and root planing is taking place. This will be done without harming collateral tissues or the tooth. Further, this will be accomplished without introducing antibiotics or resorbable delivery vectors into the system or periodontal pocket, and will allow for the immediate healing and reattachment of periodontal tissues to begin. This invention is a radical departure from all other traditional modes of periodontal therapy, as the logarithmic decrease in viable pathogenic bacteria caused by the laser exposure to the periodontal pocket is immediate and profound in conjunction with the traditional mechanical scaling. This leads to an immediate secession of inflammatory destruction and quickly let the body begin to heal the area.

BRIEF DESCRIPTION OF THE DRAWINGS

For a fuller understanding of the nature and objects of the present invention, reference is made to the following specification, which is to be taken with the accompanying drawings wherein.

DETAILED DESCRIPTION OF THE PREFERRED EMBODIMENT

Figure 1:
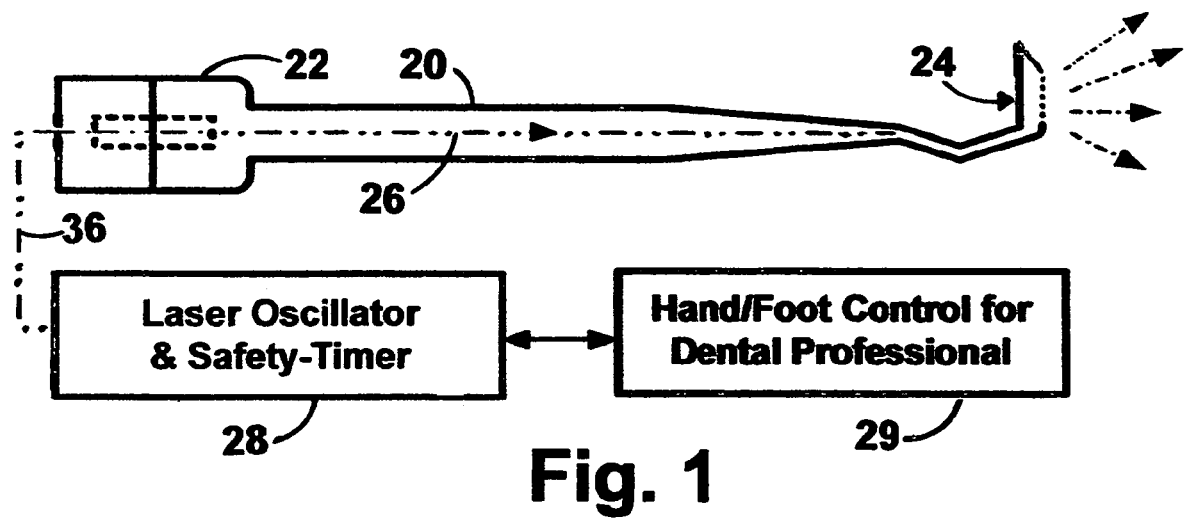
FIG. 1 is an illustration of a laser augmented periodontal scaling instrument (LAPSI) embodying the present invention.

Reasoned Basis for Laser Augmented Periodontal Scaling Instruments (LAPSI)

Any and all periodontal therapy always will consist of a best effort to arrest infection, promote healing, and maintain healthy tissue without undue damage. For the previously described armamentarium and pharmacological adjuncts to be effective in the treatment of periodontal disease and pocket elimination, a number of principles must be followed and executed, such as, proper patient positioning, knowledge of tooth morphology, correct instrument selection, correct pharmacologic choice and adaptation, and proper instrument use. When used properly, many cases of local and aggressive periodontal disease can be inhibited and reversed with these modalities. However, recent technological advances in the field of medical and dental lasers, laser delivery systems, and photo-pharmaceuticals have prompted this investigator to explore some novel applications that can be coupled to traditional hand held mechanical scalers.

This invention bypasses the need for local antimicrobial delivery and their associated problems, while turning the traditional mechanical scaler into a more effective mechanical and laser delivery device.

Specifically, this invention changes the logic and method of traditional bacterial removal from the periodontal pocket by incorporating an optical fiber into the shank of a conventional periodontal scaler. This fiber optical augmentation caries and delivers bacteriacidal solid state diode laser optical energy through the shank and exit under the blade of the scaler to all facets of the diseased pocket during the mechanical scaling procedure. This infrared optical energy delivered through the scaler exits under the blade of the scaler through a scratch and heat resistant optical quartz or sapphire window (that is the most distal aspect of the optical bundle) and bathes the periodontal tissues in the pocket at the time of the mechanical debridement. The laser energy preferably ranges from 600 nm to 1060 nm in the near infrared spectrum and is used to promote selective bacterial death. This is accomplished through intracellular bacterial chromophore targeting, bacterial targeting with local delivery of liquid exogenous chromophores and/or generalized bacterial thermolysis in the periodontal pocket by the conversion of optical laser energy to local and controlled heat energy.

It has already been established that diode fiber laser debridement in conjunction with mechanical scaling (with and without an exogenous chromophore) is an effective adjunctive treatment modality for periodontal disease. This invention in coupling the diode laser array to the scalers with an impregnated optical fiber simultaneously accomplishes two tasks during the periodontal therapy. The laser augmented scaling instruments effectively removes 99% of the pathogenic bacteria from the periodontal pocket (effectively eliminating and stopping the inflammatory response) while the traditional scaling and root planing is taking place. This is done without harming collateral tissues or the tooth. Further, this is accomplished without introducing antibiotics or resorbable delivery vectors into the system or periodontal pocket, and allows for the immediate healing and reattachment of periodontal tissues to begin.

This invention is a departure from traditional modes of periodontal therapy, as the logarithmic decrease in viable pathogenic bacteria caused by the laser exposure to the periodontal pocket is immediate and profound in conjunction with the traditional mechanical scaling. This leads to an immediate secession of inflammatory destruction and quickly lets the body begin to heal the area.

Background for Laser Assisted Bacterial Elimination in the Periodontal Pocket

The basic laws of thermodynamics state that the exchange and transfer of energy need to happen in at least two ways, with one of the ways being heat transfer. The heat deposition from the absorption of optical infrared energy exploited in this invention is to be used specifically as an adjunctive method for bacterial elimination in the periodontal pocket and other periodontal or periimplant disease entities. Solid state diode lasers in the low infrared spectrum 600 nm to 1100 nm have been used for a variety of purposes in medicine and dentistry because of their preferential absorption curve to melanin, hemoglobin, and pigmented bacteria in a biological system. Because of the poor absorption in water of this spectrum of infrared radiation, the penetration of the radiant energy in biological tissues is great. This characteristic of poor absorption to the chromophore of water and deep penetration to the tissues make it an excellent spectrum for this invention s unique need. Because of these unique characteristics, the diode near infrared laser energy being delivered from the Laser Augmented Periodontal Scaling Instruments of the present invention are able to fully penetrate the periodontal pocket, cementum, and surrounding bony architecture to accomplish its goal of bacterial elimination.

To accomplish bacterial cell death with near infrared lasers in a local biological system (the periodontal pocket), the operator has a very narrow therapeutic window of opportunity because of the heat deposition properties and characteristics of the near infrared radiation. Normal human temperature is 37° C., and this temperature corresponds to rapid bacterial growth curves in the periodontal pocket and surrounding tissue. When near infrared radiant energy is applied to the biological system, the temperature of the lazed area begins to immediately rise. With each 10° C. rise in temperature, there is a potential increase in the deleterious effects to the biological entity being treated. At 45° C., there is moderate tissue hyperthermia; at 50° C. there is a reduction in enzyme activity and cellular immobility; at 60° C. there is a denaturation of proteins and collagen with beginning coagulation; at 80° C. there is a permeabilization of cell membranes; at 100° C. there is vaporization of water and biological matter. If there is any significant duration of time that the temperature increase is at or beyond the 80° C. mark (5 to 10 sec) in the periodontal pocket, there will be irreversible and unwanted harm to the healthy periodontal structures.

To kill bacteria through the process of photothermolysis (heat induced death), a significant temperature increase must occur in the periodontal tissues for a given amount of time because all of the tissues are in proximity to or invaded by the pathogenic bacteria. Most pathogenic periodontal bacteria will continue to grow unabated until the local system hits the 50° C. mark whereupon the bacterial growth curve begins to slow down. At 60° C. bacterial growth begins to stop in a marked fashion. From 60° C. to 80° C. is the range that must be reached for time dependent exposure to result in bacterial death. This is the window of opportunity to kill the bacteria in an infected periodontal pocket without also causing irreversible heat induced damage (5 to 10 seconds at 60° C. to 80° C.) to the surrounding periodontal tissues.

This logic (photothermolysis) will work well with any of the conventional dental diode lasers currently on the market. They are easily available and function at the wavelengths of 810 nm, 830 nm, and/or 980 nm. Because each of these wavelengths is essentially transparent to the bacteria (proven with optical tweezer studies), photothermolysis is the method by which bacterial death will occur.

To expand the therapeutic window and margin of safety with the currently available conventional dental diode lasers coupled to the augmented periodontal scalers in this invention, local delivery of the chromophore Indocyanine Green (ICG) in solution, can be placed in the periodontal pocket to selectively target the pathogenic bacteria. ICG has an absorption peak at 810 nm. If used in the periodontal pocket and surrounding tissues for direct bacterial chromophore targeting, the operator of a Laser Augmented Periodontal Scaler can turn down the power and increase the exposure time in the area of treatment with the laser to gain bacterial death through thermolysis. This can occur because the ICG targeted bacteria preferentially absorb the radiant energy at wavelengths from 800 nm to 840 nm and convert the optical energy to local heat energy in the pathogenic bacteria. This cannot occur with the 980 nm dental diode laser, and more care will need to be taken by the operator of this laser.

Another diode laser applicable to the present invention allows the operator to turn down the power and increase the exposure time in the area of treatment with the laser on, to gain bacterial death. That is a dual wavelength (870 nm and 930 nm) diode laser. This laser is designed to kill bacteria with a photodamage instead of a photothermal effect. This occurs because the wavelengths (870 nm and 930 nm) are not transparent to the bacteria and react with one or more bacterial intra-cellular chromophores or pigments to damage the bacterial cell and induce death. This laser, when coupled to a periodontal scaler, does not require ICG to expand its therapeutic window, as it is already selectively targeting bacterial chromophores, and kills the bacteria by photodamage long before photothermolysis takes place.

As the above logical progression explains, Laser Augmented Periodontal Scaling Instruments can be used with, and coupled to, any existing diode laser that a practitioner may already have. By the practitioners-simply understanding the unique physics and photobiology of his/her existing laser, and adjusting the settings and technique, successful, safe and predictable bacterial elimination can be achieved in most cases with this invention.

Mechanical Specifications of the Invention

Dental instruments are designed for the purpose of removing calculus and plaque, root planing, and removing diseased soft tissues from the periodontal pocket.

The instruments of the present invention generally comprise (1) a shank which is to be hand held and manipulated by a dental professional during an operation, (2) at least one working end which presents, in contiguity, a laser optical head and a mechanical cutting head that simultaneously address a surgical site, and (3) a fiber optic laser bundle that extends from an optical input at one end of the shank, at which a laser is fitted, to an optical output at the other end of the shank, at which laser energy is delivered. The arrangement is such that, during an operation, the dental professional can subject the surgical site simultaneously to (1) mechanical cutting, scraping and grinding, and (2) laser trimming and cauterization.

Generally, the shank is composed of stainless steel, high carbon steel, and/or autoclaveable high strength plastic (for implants). The laser connects through an interchangeable fitting to a conventional the fiber optic bundle in or at the shank. The fiber optic bundle, when located in the shank, allows optical energy to exit in contiguity with the bead through a heat and scratch resistant quartz window, where, upon exit, it bathes the surgical site, e.g., the periodontal packet and tissues, with diode laser energy.

Figure 2:
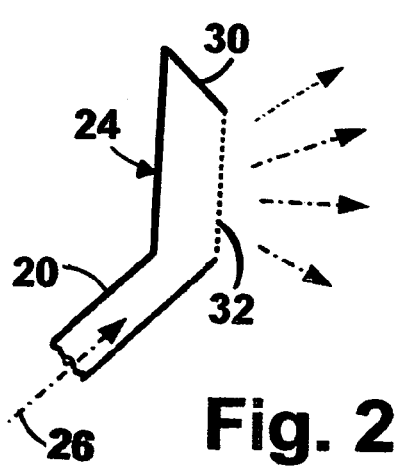
FIG. 2 is a broken-away illustration showing details of the head of the instrument of FIG. 1.

FIG. 1 illustrates a curette comprising, in accordance with the present invention: a hollow shank 20 having a rearward interchangeable fitting 22, and a forward contact head 24. Within shank 20 extends a fiber optic bundle 26. As shown, laser energy 36 is delivered from a safety-timed laser oscillator 28 through interchangeable fitting 22 and laser bundle 26 to contact head 24 under hand/foot control 29. As shown in FIG. 2, in contiguity at contact head 24 are a blade 30 and an exit window 32.

Figure 3:
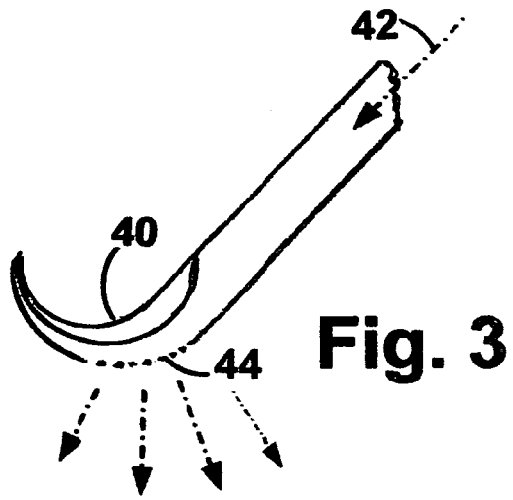
FIG. 3 is a broken-away illustration showing details of one embodiment of a blade of the instrument of FIG. 1.
Figure 4:
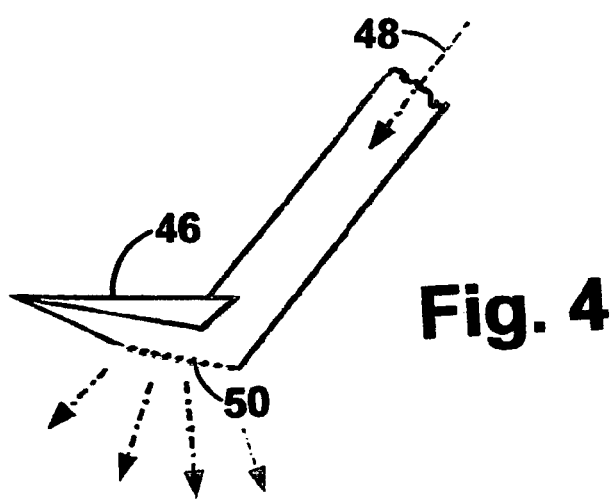
FIG. 4 is a broken-away illustration showing details of another embodiment of a blade of the instrument of FIG. 1.

As shown in FIGS. 3 and 4, respectively, one embodiment of the blade is curved as at 40, and another embodiment of the blade is linear as at 46. In the embodiment of FIG. 3, fiber optic bundle 42 and window 44 closely underly the cutting edge of the blade. In the embodiment of FIG. 4, fiber optic bundle 48 and window 50 closely underly the cutting edge of the blade. Each of the scalers of FIGS. 3 and 4 has an interchangeable fitting that is analogous to interchangeable fitting 22 for optional and interchangeable interconnection with the mating fitting that communicates with the laser oscillator.

OPERATION

In operation, utilization of an instrument embodying the present invention enables a dental professional to subject a surgical site simultaneously to (1) mechanical cutting, scraping and grinding, and (2) laser trimming and cauterization. As a result, simultaneous removal of diseased tissue and destruction of residual bacteria is enabled.

What is claimed is:

1. A process for performing dental surgery with an instrument, wherein the instrument includes:
    (a) a hollow shank having, a rearward fitting, and a forward head including a contact region and a window in proximity thereto;
    (b) said contact region being adapted for cutting, scraping, and/or grinding dental tissue;
    (c) a source of laser energy, wherein the source is configured and arranged to produce laser energy for photodamage or photothermal effect to destroy residual bacteria;
    (d) said window being transmissive with respect to said laser energy; and
    (e) a fiber optic bundle extending from said source of laser energy, through said fitting and said shank for communication with said window;
    said dental process comprising applying said instrument to subject a surgical site simultaneously to
    (1) mechanical cutting, scraping and/or grinding, and
    (2) said laser energy for photodamage or photothermal effect, to remove diseased tissue and to destroy residual bacteria; wherein said laser energy is generated by at least one diode laser configured and arranged to produce an output including 870 nm or 930 nm or both.

2. The process of claim 1, further comprising trimming and cauterizing to remove diseased tissue and to destroy residual bacteria.

* * * * *